(12) United States Patent
Thompson

(10) Patent No.: US 7,582,418 B2
(45) Date of Patent: Sep. 1, 2009

(54) ANTIMICROBIAL CHELATES

(75) Inventor: Robert Charles Thompson, Peterson, UT (US)

(73) Assignee: Albion Laboratories, Inc., Clearfield, UT (US)

( * ) Notice: Subject to any disclaimer, the term of this patent is extended or adjusted under 35 U.S.C. 154(b) by 0 days.

(21) Appl. No.: 11/718,482

(22) PCT Filed: Nov. 3, 2005

(86) PCT No.: PCT/US2005/040010

§ 371 (c)(1), (2), (4) Date: May 2, 2007

(87) PCT Pub. No.: WO2006/135445

PCT Pub. Date: Dec. 21, 2006

(65) Prior Publication Data

US 2007/0293466 A1    Dec. 20, 2007

Related U.S. Application Data

(60) Provisional application No. 60/624,682, filed on Nov. 3, 2004.

(51) Int. Cl.
*C12Q 1/00* (2006.01)
*A61K 8/27* (2006.01)

(52) U.S. Cl. .............. 435/4; 424/67; 514/184

(58) Field of Classification Search .............. None
See application file for complete search history.

(56) References Cited

U.S. PATENT DOCUMENTS

| | | |
|---|---|---|
| 944,738 A | 12/1909 | Loose |
| 1,488,097 A | 3/1924 | Creger |
| 1,765,867 A | 6/1930 | Granger |
| 1,861,189 A | 5/1932 | Pasternack |
| 1,927,640 A | 9/1933 | Granger |
| 2,512,537 A | 6/1950 | Zellers |
| 2,527,686 A | 10/1950 | Sandberg |
| 2,999,752 A | 9/1961 | Webb |
| 3,341,414 A | 9/1967 | Cherkas et al. |
| 3,622,662 A | 11/1971 | Roberts et al. |
| 4,469,674 A | 9/1984 | Shah et al. |
| 4,503,070 A | 3/1985 | Eby, III |
| 4,664,906 A | 5/1987 | Sipos |
| 4,684,528 A | 8/1987 | Godfrey |
| 4,758,439 A | 7/1988 | Godfrey |
| 4,774,078 A | 9/1988 | Curtis et al. |
| 4,937,234 A | 6/1990 | Fahim |
| RE33,465 E | 11/1990 | Eby, III |
| 4,992,259 A | 2/1991 | Schiraldi et al. |
| 5,002,970 A | 3/1991 | Eby, III |
| 5,095,035 A | 3/1992 | Eby, III |
| 5,286,748 A | 2/1994 | Eby, III |
| 5,330,748 A | 7/1994 | Winston et al. |
| 5,385,727 A | 1/1995 | Winston et al. |
| 5,405,836 A | 4/1995 | Richar et al. |
| 5,409,905 A | 4/1995 | Eby, III |
| 5,455,024 A | 10/1995 | Winston et al. |
| 5,626,831 A | 5/1997 | Van Moerkerken |
| 5,875,799 A | 3/1999 | Petrus |
| 5,897,891 A | 4/1999 | Godfrey |
| 6,093,417 A | 7/2000 | Petrus |
| 6,121,315 A | 9/2000 | Nair et al. |
| 6,169,118 B1 | 1/2001 | Bilali |
| 6,242,009 B1 | 6/2001 | Batarseh et al. |
| 6,267,979 B1 | 7/2001 | Raad et al. |
| 6,288,106 B1 | 9/2001 | Pearson et al. |
| 6,316,008 B1 | 11/2001 | Godfrey |
| 6,323,354 B1 | 11/2001 | Moore |
| 6,331,559 B1 | 12/2001 | Bingham et al. |
| 6,361,312 B1 | 3/2002 | Ekanayake et al. |
| 6,475,526 B1 | 11/2002 | Smith |
| 6,558,710 B1 | 5/2003 | Godfrey |
| 6,558,723 B2 | 5/2003 | Ekanayake et al. |
| 6,607,711 B2 * | 8/2003 | Pedersen ............ 424/49 |
| 6,630,172 B2 | 10/2003 | Batarseh |
| 6,730,329 B1 | 5/2004 | Smith |
| 6,794,375 B2 | 9/2004 | Sarama et al. |
| 6,855,341 B2 | 2/2005 | Smith |
| 6,887,894 B2 | 5/2005 | Kramer et al. |
| 7,078,399 B2 | 7/2006 | Michaelis et al. |

(Continued)

FOREIGN PATENT DOCUMENTS

WO    WO 2006/135445 A2    12/2006

OTHER PUBLICATIONS

"Eby's ColdCure Zinc Acetate Lozenges, the World's Only Common Cold Cure," retrieve Oct. 27, 2004 from http://coldcure.com/ (6 pages).

(Continued)

Primary Examiner—Robert B Mondesi
Assistant Examiner—Padma V Baskar
(74) Attorney, Agent, or Firm—Christopher L. Wight; Ryan L. Marshall; Brinks Hofer Gilson & Lione

(57) ABSTRACT

Methods useful for inhibiting growth of a variety of microbes including bacteria and fungi are disclosed. The methods involve contacting a microbe with an inhibitory amount of a zinc chelate. Methods useful for preserving a consumable product are also disclosed.

5 Claims, No Drawings

U.S. PATENT DOCUMENTS

| | | | |
|---|---|---|---|
| 7,105,190 | B2 | 9/2006 | Ekanayake et al. |
| 7,435,429 | B2 * | 10/2008 | Modak et al. ............... 424/641 |
| 2001/0031744 | A1 | 10/2001 | Kosbab |
| 2002/0028796 | A1 | 3/2002 | Kramer et al. |
| 2003/0095230 | A1 | 5/2003 | Neely et al. |
| 2003/0211209 | A1 | 11/2003 | Ekanayake et al. |
| 2004/0014749 | A1 | 1/2004 | Michaelis et al. |
| 2004/0086575 | A1 | 5/2004 | Smith |
| 2004/0102429 | A1 | 5/2004 | Modak et al. |

OTHER PUBLICATIONS

"New Study Shows Zinc Lozenges Play Key Role in Preventing Colds and Shortening Colds," retrieved Oct. 27, 2004 from http:\www.quantumhealth.com/js_na/zinc_lozenges_key_role.html (1 page).

"Product Review: Zinc Supplements (Lozenges, Pills, and Liquids," retrieved Oct. 27, 2004 from http://www.consumerlab.com/results/zinc.asp (4 pages).

"Zinc Lozenges As A Cold Remedy," retrieved Oct. 27, 2004 from http://www.medicinenet.com/zinc_lozenges_as_a_cold_remedy/page2.htm (4 pages).

"Zinc Lozenges for Colds: Natural Health Care Products," retrieved Oct. 27, 2004 from http:/www.health-pages.com/zl/ (3 pages).

Andersen, G. Douglas, "Zinc Lozenges and the Common Cold," 15(1) *Dynamic Chiropractic*, Jan. 1, 1997, http://www.chiroweb.com/archives/15/01/08.html, 4 pages (Oct. 27, 2004).

Cold-Eeze cold drop lozenges, 2 pages (Nov. 29, 2004).

Target™ brand Zinc Gluconate Glycine lozenges, 2 pages (Nov. 29, 2004).

Stier, Roger E., "A Taste Receptor Blocker for Oral Hygiene Compositions," http://www.thecosmeticsite.com/formulating/toiletries/959676.html, 5 pages (Oct. 25, 2004).

* cited by examiner

ANTIMICROBIAL CHELATES

CROSS REFERENCE TO RELATED APPLICATION

This application claims the benefit of the filing date of U.S. Provisional Patent Application No. 60/624,682, filed Nov. 3, 2004, the disclosure of which is incorporated, in its entirety, by this reference.

TECHNICAL FIELD OF THE INVENTION

The present invention relates to antimicrobial chelate compounds, compositions, and methods of administering and preparing the same.

BACKGROUND OF THE INVENTION

Sporadic outbreaks of illness resulting from microbial contamination of food products are a continuing source of medical and public health concern. Pathogens such as bacteria, fungi, viruses, and bacterial spores are responsible for a plethora of human and animal ills, as well as contamination of food and biological and environmental samples. Microbial infections generally begin with attachment or colonization in mucus membranes followed by subsequent invasion and dissemination of the infectious microbe. The portals of entry of pathogenic microbes include mucus membranes and the digestive tract. Food preparations whether for human consumption or for livestock feed are prone to microbial contamination and can often introduce the human or animal tissue.

Accordingly, there continues to be a need to inhibit microbial growth in food stocks. There is also a simultaneous need to provide antimicrobial assistance to humans and animals infected by pathogenic microbes. The present invention provides antimicrobial compounds and compositions useful in inhibiting growth of microbes.

SUMMARY OF THE INVENTION

The methods of the present invention are useful for inhibiting growth of a variety of microbes. The invention provides a method of inhibiting microbial growth by contacting one or more microbes with an inhibitory amount of a zinc chelate. The invention also provides a method for preserving a consumable product by contacting the consumable product with a compound which inhibits microbial growth such as zinc chelate. The invention further provides a method for preventing the growth of microbes on a food product by contacting the food product with a microbial growth inhibiting effective amount of a zinc chelate.

In some embodiments, the zinc chelate can be selected from zinc lipoate, zinc gluconate and zinc amino acid chelate. In some embodiments, the zinc chelate can be selected from zinc lipoate and zinc amino acid chelate. In some embodiments, the zinc chelate can be zinc bisglycinate. In some embodiments, the zinc chelate can be a zinc amino acid chelate. In some embodiments, the microbe can be a bacterium. In other embodiments, the microbe can be a fungus. In still other embodiments, the microbes can include both bacteria and fungi.

The methods of the present invention are useful for inhibiting growth of a variety of bacteria. The invention provides a method of inhibiting bacterial growth by contacting one or more bacterium with an inhibitory amount of a zinc chelate. The invention also provides a method for preserving a consumable product by contacting the consumable product with a compound which inhibits bacterial growth such as a zinc chelate. The invention further provides a method for preventing the growth of bacteria on a food product by contacting the food product with a bacterial growth inhibiting effective amount of a zinc chelate.

In some embodiments, the zinc chelate can be selected from zinc lipoate, zinc gluconate and zinc amino acid chelate. In some embodiments, the zinc chelate can be selected from zinc lipoate and zinc amino acid chelate. In some embodiments, the zinc chelate can be zinc bisglycinate. In some embodiments, the zinc chelate can be a zinc amino acid chelate. In some embodiments, the bacteria which are inhibited can be Gram-negative bacteria and/or Gram-positive bacteria.

The invention provides a method of inhibiting fungal growth by contacting one or more fungi with an inhibitory amount of a zinc chelate. The invention also provides a method for preserving a consumable product by contacting the consumable product with a compound which inhibits fungal growth such as a zinc chelate. The invention further provides a method for preventing the growth of fungus on a food product by contacting the food product with a fungal growth inhibiting effective amount of a zinc chelate.

In some embodiments, the zinc chelate can be selected from zinc lipoate, zinc gluconate and zinc amino acid chelate. In other embodiments, the zinc chelate can be selected from zinc lipoate and zinc amino acid chelate. In other embodiments, the zinc chelate is zinc bisglycinate. In yet other embodiments, the zinc chelate can be a zinc amino acid chelate.

DETAILED DESCRIPTION OF THE INVENTION

The term "chelate" as used herein means a molecular entity made up of a central metal associated with at least one bidentate ligand and optionally associated with one or more mono- or multi-dentate ligands. In the interaction between the central metal and any of the ligands, the bonds between the ligand and the central metal can include covalent bonds, ionic bonds, and/or coordinate covalent bonds.

The term "chelate ring" as used herein means the atoms of the ligand and central metal form a heterocyclic ring. In the interaction between the central metal and a multidentate ligand, one or more chelate rings of from 3 to 8 members can exist. The chelate ring can be of from 5 to 6 members.

The term "ligand" as used herein means a molecular group that is associated with a central metal atom. The terms monodentate, bidentate (or didentate), tridentate, tetradentate, and multidentate are used to indicate the number of potential binding sites of the ligand. For example, a carboxylic acid can be a bidentate or other multidentate ligand because it has at least two binding sites, the carboxyl oxygen and hydroxyl oxygen. In like manner, an amide has at least two binding sites, the carboxyl oxygen and the nitrogen atom. An amino sugar can have at least two binding sites and many amino sugars will have multiple binding sites including the amino nitrogen, a hydroxyl oxygen, an ethereal oxygen, an aldehyde carbonyl, and/or a ketone carbonyl. The term ligand includes amino acids such as the naturally occurring amino acids.

The term "metal" as used herein means any alkaline, alkaline earth, transition, rare earth, basic, and semi-metals which can coordinate with a ligand. Representative metals include the transition metals, lanthanide, and actinide metals. In some embodiments, the metal has d-orbitals capable of interacting with a ligand. The oxidative state of the metal can vary from 0 to 8.

The term "nutritionally acceptable metal" as used herein means metals that are known to be needed by living organisms, particularly plants and mammals, including humans. Metals such as boron, calcium, chromium, cobalt, copper, iron, magnesium, manganese, potassium, selenium, vanadium, and zinc, among others, are examples of nutritionally acceptable metals.

The terms "hydrate" or "n-hydrate" as used herein means a molecular entity with some degree of hydration, where n is an integer representing the number of waters of hydration, e.g., monohydrate, dihydrate, trihydrate, tetrahydrate, pentahydrate, hexahydrate, septahydrate, octahydrate, nonahydrate, etc.

The term "microbe" or "microbes" as used herein means a prokaryotic or eukaryotic organism, particularly a bacterium or fungi.

An "amino acid chelate" as used herein means the product resulting from the reaction of a metal or metal ion from a soluble metal salt with one or more amino acids having a mole ratio of from 1:1 to 1:4, or, in particular embodiments, having a mole ratio 1:2, moles of metal to moles of amino acids, to form coordinate covalent bonds. The average weight of the hydrolyzed amino acids is approximately 150 and the resulting molecular weight of the chelate will typically not exceed a molecular weight of about 800 amu and more frequently less than about 1000 amu. The chelate products can be identified as by the specific metal forming the chelate, e.g., iron amino acid chelate, copper amino acid chelate, etc.

The reason a metal atom can accept bonds over and above the oxidation state of the metal is due to the nature of chelation. For example, at the α-amino group of an amino acid, the nitrogen contributes both lone-pair electrons used in the bonding to the metal. These electrons fill available spaces in the d-orbitals of the metal forming a coordinate covalent bond. Thus, a metal ion with a normal valency of +2 can be bonded by up to eight bonds when fully chelated. In this state, the unfilled orbitals in the metal can be satisfied by both bonding electrons from lone pair electrons as well as electrons from ionic species. The chelate can be completely satisfied by the bonding electrons and the charge on the metal atom (as well as on the overall molecule) can still be zero. As stated previously, it is possible that the metal ion be bonded to the carboxyl oxygen by either coordinate covalent bonds or ionic bonds. However, the metal ion can also be bonded to the α-amino group by coordinate covalent bonds only.

Amino acid chelates can also be formed using peptide ligands instead of single amino acids. These will usually be in the form of dipeptides, tripeptides, and sometimes, tetrapeptides because larger ligands have a molecular weight which is too great for direct assimilation of the chelate formed. Generally, peptide ligands will be derived by the hydrolysis of protein. However, peptides prepared by conventional synthetic techniques or genetic engineering can also be used. When a ligand is a di- or tri-peptide, a radical of the formula $[C(O)CHR_1NH]_g$ H will replace one of the hydrogens attached to the nitrogen atom on an amino acid ligand. $R_1$ can be H or the residue of any other naturally occurring amino acid and g can be an integer of 1, 2 or 3. When g is 1, the ligand will be a dipeptide, when g is 2, the ligand will be a tripeptide, and so forth.

In some embodiments, the ligand can be any ligand capable of forming a chelate with a metal. Ligands can include those with primary and/or secondary amines. Ligands can also include amino acids with primary amines. Ligands can also include primary or secondary amines each with a carboxylic acid β to the primary or secondary amine. Such ligands include but are not limited to the α-amino acids selected from the naturally occurring amino acids alanine, arginine, asparagines, aspartic acid, cysteine, glutamic acid, glutamine, glycine, histidine, isoleucine, leucine, lysine, methionine, phenylalanine, proline, serine, threonine, tryptophan, tyrosine, and valine. Other ligands include the amino acids 4-hydroxyproline, 5-hydroxylysine, homoserine, homcysteine, ornithine, β-alanine, γ-aminobutyric acid (GABA), statine, ornithine, and statin. In some embodiments, the amino acid is selected from the non-natural amino acids. In some embodiments, the amino acid is selected from the aliphatic naturally occurring amino acids selected from alanine, glycine, isoleucine, leucine, proline, and valine. Where the R side chain of an amino acid has a functional group which would be more nucleophilic than the primary amine of the amino acid, then a protecting group can be present on that side chain functional group. For example, the primary amine of the R side chain for lysine may be protected by formaldehyde prior to addition of a chromophore. The term ligand thus includes modified ligands which may also called protected ligands. Amino acids ligands can be the L-amino acids, the D-amino acids, or a racemic mixture of both types. In some embodiments, the amino acids are the L-amino acids.

Chelation can be confirmed and differentiated from mixtures of components by infrared spectra through comparison of the stretching of bonds or shifting of absorption caused by bond formation. The following examples illustrate the antimicrobial activity of metal chelates in supplementing feed stocks in animals as well as nutritional supplements in humans.

EXAMPLES

Two methods were used to examine whether an inhibitory effect from the zinc containing compounds was observable and if there was an inhibitory effect, whether the effect was bactericidal (bacteria-killing) or bacteriostatic (bacterial-inhibiting) in nature. In the first method, two Gram-positive bacteria strains (*Staphlococcus aureus, Streptococcus pyogenes*), two Gram-negative bacteria strains (*Salmonella typhimerium, Eschrichia coli*), and one common yeast strain (*Candida albicans*) were grown nutrient agar plates, except in the case of *S. pyogenes* which was grown on blood agar plates. The zinc containing compounds 1-7 listed in Table 1 were tested. Compounds 8-18 were used as controls.

TABLE 1

| Sample # | Compound | % Zn |
|---|---|---|
| 1 | Zinc Chloride | 46.5% |
| 2 | Zinc Citrate | 32.3% |
| 3 | Zinc Acetate | 29.5% |
| 4 | Zinc Sulfate | 22.7% |
| 5 | Zinc Bis-Glycinate | 21.2% |
| 6 | Zinc Lipoate | 14.4% |
| 7 | Zinc Gluconate | 12.9% |
| 8 | Neomycin | 0.0% |
| 9 | Ciproflaxicin | 0.0% |
| 10 | Amoxicillin | 0.0% |
| 11 | Tetracycline | 0.0% |
| 12 | Sulfamethoxazole | 0.0% |
| 13 | Vancomycin | 0.0% |
| 14 | Sodium Chloride | 0.0% |
| 15 | Sodium Acetate | 0.0% |
| 16 | Sodium Glycinate | 0.0% |
| 17 | Sodium Sulfate | 0.0% |
| 18 | Sodium Citrate | 0.0% |

Zone inhibition assays were conducted with eighteen different samples in accordance with the methodology described by Maruzella, J. C. and Henry, P. A., J. Am. Pharm. Assoc.

47:894 (1958) for filter paper disc area diffusion. Sample solutions were prepared to approximate 100 mg/mL concentrations.

Organisms were grown for 24 hours at 37° C. on blood agar plates with the exception of Candida albicans which was grown in a standard methods agar (SMA) medium. Solutions of each sample were prepared using sterile DD water at a concentration of 100 mg/ml. Paper discs were saturated with solution from each sample and dried aseptically. Control discs were obtained from BD Diagnostic Systems Sparks, Md., USA (BBL™ Sensi-Disc™) for neomycin (30 μg), ciproflaxicin (5 μg), amoxicillin (30 μg), tetracycline (30 μg), sulfamethoxazole (23.75 μg) and vancomycin (30 μg). Following drying of solution derived discs, all discs were placed on agar plates with each of the five different microorganisms. The organisms were grown for 24 hours at 37° C. and then inhibitory zones were measured as the distance from the edge of the disc to the point where bacteria were observed to grow. The inhibitory zone measured in millimeters for each sample is listed in Table 2.

TABLE 2

| Sample # | Eschrichia coli | Staphlococcus aureus | Salmonella typhimerium | Candida albicans | Streptococcus pyogenes |
|---|---|---|---|---|---|
| 1 | 4 | 6 | 3.5 | 4.5 | 2.5 |
| 2 | 1.5 | 1 | 2 | no activity | 3.5 |
| 3 | 3 | 2 | 3 | 2 | 3.5 |
| 4 | 3.5 | 3.7 | 3 | 2 | 2 |
| 5 | 3.5 | 3.5 | 3.5 | 0.5 | 4 |
| 6 | .5 | 1.5 | 2 | no activity | 1 |
| 7 | 2 | 3 | 2.75 | no activity | 5 |
| 8 | 3 | 6 | 6 | no activity | 3 |
| 9 | 5 | 8.5 | 10 | no activity | 3 |
| 10 | 3.5 | 7.5 | 8 | no activity | 12.5 |
| 11 | 5.5 | 7.5 | 7 | no activity | no activity |
| 12 | 3 | 3.5 | 4 | no activity | 7.5 |
| 13 | no activity | 5 | no activity | no activity | 5 |
| 14 | no activity | no activity | no activity | no activity | no activity |
| 15 | no activity | no activity | no activity | no activity | no activity |
| 16 | no activity | no activity | no activity | no activity | no activity |
| 17 | no activity | no activity | no activity | no activity | no activity |
| 18 | no activity | no activity | no activity | no activity | no activity |

In the second method, turbidity assays were conducted. Tryptic soy broth (TSB) tubes were inoculated with 1.0 mL of sample solutions (100 mg/mL) and 50 μL of 24-hour cultures of each microbe. In the case of C. albicans, 100 μL of 24-hour culture was used. After 24 hours, an aliquot from each tube was plated out onto nutrient media and incubated for 24 hours. Following incubation, colonies on each plate were observed and characterized as one of three categories: no-growth (NG) which corresponds with excellent inhibitory activity, partial growth (PG) which corresponds with good inhibitory activity, complete growth (CG) which corresponds with little or no inhibitory activity. Those samples that were controls are designated as "Con." Observed data is listed in Table 3.

TABLE 3

| Sample # | Staphlococcus aureus | Salmonella typhimerium | Candida albicans | Eschrichia coli |
|---|---|---|---|---|
| 1 | PG | NG | PG | PG |
| 4 | CG | CG | CG | CG |
| 5 | PG (1) | PG | NG | NG |
| 12 | CG | CG | CG | CG |
| 15 | NG | PG | CG | NG |

S. pyongenes, could not be grown in the solution, so the turbidity assay was not conducted for that microorganism. When the data from both zone inhibition (Table 2) and turbidity (Table 3) assays are compared, an indication of the inhibition activity may be evident. When a zone of inhibition was observed and no growth was observed in the turbidity assay, then the sample indicates microbicidal properties. When a zone of inhibition was observed with partial growth in the turbidity assay, then the sample displays microbiostatic properties.

The data shows that zinc salts and zinc chelates display antimicrobial activity and the antimicrobial activity is derived more from the zinc metal than the ligand as the sodium salts of the ligands displayed no activity. Thus, the data demonstrates that zinc chelates display antimicrobial activity.

I claim:

1. A method of inhibiting microbial growth comprising the step of contacting one or more microbes with an amount of a zinc chelate sufficient to inhibit the one or more microbes, wherein the zinc chelate is selected from zinc lipoate, and zinc bisglycinate.

2. The method of claim 1, wherein the one or more microbes are bacteria.

3. The method of claim 1, wherein the one or more microbes are fungi.

4. The method of claim 1, wherein the one or more microbes are selected from bacteria and fungi.

5. The method of claim 1, wherein the one or more microbes are selected from Staphylococcus aureus, Streptococcus pyogenes, Salmonella typhimerium, and Eschrichia coli, and Candida albicans.

* * * * *